(12) United States Patent
Lorenz

(10) Patent No.: US 6,616,707 B2
(45) Date of Patent: Sep. 9, 2003

(54) PROCESS AND COMPOSITION FOR THE OXIDATIVE DYEING OF HUMAN HAIR

(75) Inventor: Heribert Lorenz, Gross-Bieberau (DE)

(73) Assignee: Goldwell GmbH, Darmstadt (DE)

(*) Notice: Subject to any disclaimer, the term of this patent is extended or adjusted under 35 U.S.C. 154(b) by 0 days.

(21) Appl. No.: 09/809,931

(22) Filed: Mar. 16, 2001

(65) Prior Publication Data

US 2001/0037531 A1 Nov. 8, 2001

(30) Foreign Application Priority Data

Apr. 1, 2000 (DE) .......................... 100 16 497

(51) Int. Cl.$^7$ ................................. A61K 7/13
(52) U.S. Cl. .................... 8/405; 8/406; 8/407; 8/408; 8/409
(58) Field of Search ................. 8/404, 405, 406, 8/407, 408, 409, 401

(56) References Cited

U.S. PATENT DOCUMENTS

| | | | | |
|---|---|---|---|---|
| 4,992,077 A | * | 2/1991 | Tennigkeit et al. | 8/406 |
| 5,006,127 A | * | 4/1991 | Tennigkeit et al. | 8/406 |
| 5,431,698 A | * | 7/1995 | Tennigkeit et al. | 8/408 |
| 5,540,738 A | * | 7/1996 | Chan et al. | 8/406 |
| 5,716,418 A | * | 2/1998 | Matzik et al. | 8/406 |
| 5,792,220 A | * | 8/1998 | Wenke et al. | 8/409 |
| 5,961,667 A | * | 10/1999 | Doehling et al. | 8/408 |

FOREIGN PATENT DOCUMENTS

| | | | | |
|---|---|---|---|---|
| DE | 35 30 271 | | 2/1987 | |
| DE | 36 28 397 | | 2/1988 | |
| DE | 36 28 398 | | 2/1988 | |
| DE | 40 18 259 | | 12/1991 | |
| DE | 42 27 864 | | 2/1994 | |
| EP | 0 642 783 | | 8/1994 | |
| JP | 06 180565 | | 7/1994 | |
| JP | 07149618 A | * | 6/1995 | A61K/7/13 |
| JP | 08026943 | * | 1/1996 | |

* cited by examiner

Primary Examiner—Mark Kopec
Assistant Examiner—Eisa Elhilo
(74) Attorney, Agent, or Firm—Norris McLaughlin & Marcus

(57) ABSTRACT

The invention concerns a process for the oxidative dyeing of human hair, whereby an aqueous composition having a pH-value between 7.0 and 12.0 is applied to the hair, wherein this Composition (AB) was obtained by admixture of an oxidation dyestuff precursor Composition (A), which comprises at least one developing and at least one coupling substance as well as at least one or more specific metal compounds, having an alkaline pH-value, with a hydrogen peroxide Composition (B), having a pH-value in the acidic range and comprising 0.05 & to 5.0% by weight, calculated to the total composition, of 1-hydroxyethane-1,1-diphosphonic acid and/or the alkali or ammonium salts thereof.

14 Claims, No Drawings

PROCESS AND COMPOSITION FOR THE OXIDATIVE DYEING OF HUMAN HAIR

BACKGROUND OF THE INVENTION

The present invention concerns a process for the intensive dyeing of human hair with the use of oxidative hair dyeing compositions and a composition for carrying out this procedure.

EP 642 783 A1 already discloses a hair dyeing composition on the basis of oxidation dyestuff precursors, which dyes the hair within a reduced processing time while simultaneously brightening the hair, and which contains at least one defined metal salt and at least one ammonium compound, selected from the group ammonium chloride, ammonium sulfate, ammonium carbonate, ammonium bicarbonate and ammonium carbamate, and wherein the ready-to-use mixture has a pH-value between 8 and 11, preferably 9 and 10 after admixture with an oxidizing agent.

This invention constitutes a further development of the procedures and compositions disclosed in DE 35 30 271 C2, DE 36 28 397 C2 and DE 36 28 398 C2 for the oxidative dyeing of human hair, where coloration takes place at a pH-value between 5.9 and 6.9, and wherein a satisfactory coloration is only possible because of the addition of small amounts of metal compounds, in particular manganese dioxide, potassium iodide, calcium chloride and magnesium salts, resulting in a slightly acidic composition.

Proposals have also been made to carry out the coloration under addition of these metal compounds in an alkaline range, in order to achieve more intensive colorations while simultaneously reducing the processing time of the hair-dyeing mixture applied onto the hair. However, the reactions in an alkaline medium proved to be so fast that mixing the oxidation dyestuff precursor with the oxidizing agent, normally hydrogen peroxide, results in an intense foaming activity, in consequence of which the mixture cannot be duly applied to the hair.

SUMMARY OF THE INVENTION

It has now been found that this effect can be prevented by mixing an aqueous oxidation dyestuff precursor Composition (A), containing at least one developing and at least one coupling substance comprising at least one metal compound, selected from manganese dioxide, potassium iodide, sodium iodide, lithium chloride, calcium chloride, calcium nitrate, magnesium chloride, magnesium acetate, barium nitrate, barium chloride, copper(II) chloride, copper(II) sulfate, cobalt chloride, iron oxide, iron chloride, cerium sulfate, vanadium sulfate, potassium bichromate and/or sodium bichromate and having an alkaline pH-value, with an aqueous hydrogen peroxide composition (B) having an acidic pH-value and comprising 0.05% to 0.5% by weight, calculated to the total composition, of 1-hydroxyethane-1,1-diphosphonic acid and/or the alkali or ammonium salts thereof, whereby the ready-to-use hair-dyeing mixture has a pH-value ranging between 7 and 12. It is thereby possible to obtain an intensive, stable hair coloration without undesirable side-effects.

Object of the invention is also a composition for the oxidative dyeing of human hair, consisting of two aqueous Compositions A and B stored separately until application, whereby the Composition A comprises at least one developing and one coupling substance, as well as at least one or more metal compounds, selected from manganese dioxide, potassium iodide, sodium iodide, lithium chloride, calcium chloride, calcium nitrate, magnesium chloride, magnesium acetate, barium nitrate, barium chloride, copper(II) chloride, copper(II) sulfate, cobalt chloride, iron oxide, iron chloride, cerium sulfate, vanadium sulfate, potassium bichromate and/or sodium bichromate, having an alkaline pH-value, and the Composition B comprises hydrogen peroxide and 0.1% to 5% by weight, calculated to the total composition, of 1-hydroxyethane-1,1-diphosphonic acid and/or the alkali or ammonium salts thereof, having an acidic pH-value, whereby mixing of these Compositions A and B results in a hair-dyeing composition with a pH-value between 7.0 and 12.0.

DESCRIPTION OF THE PREFERRED EMBODIMENT

The proportion of 1-hydroxyethane-1,1-diphosphonic acid (HEDP) in the acidic hydrogen peroxide composition preferably is from about 0.1% to 2.5%, in particular about 0.2% to 1% by weight, calculated to the total composition. The pH-value thereof ranges in particular between about 1.5% to 5%, preferably 2% to 4%. Suitable salts of HEDP are in particular the sodium and ammonium salts thereof.

The proportion of the metal compounds in the oxidation dyestuff precursor composition is in particular from about 0.0005% to about 1%, preferably about 0.001% to 0.5%, especially preferred about 0.005% to 0.25% by weight, calculated to the total composition selected from manganese dioxide, potassium iodide, sodium iodide, lithium chloride, calcium chloride, calcium nitrate, magnesium chloride, magnesium acetate, barium nitrate, barium chloride, copper (II) chloride, copper(II) sulfate, cobalt chloride, iron oxide, iron chloride, cerium sulfate, vanadium sulfate, potassium bichromate and/or sodium bichromate.

Especially preferred are manganese dioxide, potassium iodide, sodium iodide, copper(II) chloride, copper(II) sulfate, calcium chloride and/or calcium nitrate.

The incorporated oxidation dyestuff precursor mixtures, being adjusted to an alkaline pH-value, and each comprising at least one developing and one coupling substance as well as an oxidizing agent, are known per se.

With regard to these ready-to-use mixtures (i.e. containing the peroxide), having a pH-value between about 7 and 12, preferably 9 and 10, especially about 9.5, reference is made to the state of the art, for example to the monography of K. Schrader, "Grundlagen und Rezepturen der Kosmetika", $2^{nd}$ Ed., pages 784 to 804 (1989); the products disclosed therein are useful within the scope of the procedure according to the invention, as are the additional developing and coupling substances and shading agents also known from the prior art.

Examples of developing substances are in particular 1,4-diaminobenzene, 2,5-diaminotoluene, tetraamino pyrimidine, triaminohydroxy pyrimidines, 1,2,4-triaminobenzene, 2-(2,5-diaminophenyl)ethanol, 2-(2'-hydroxyethyl amino)-5-aminotoluene, 1-amino-4-bis-(2'-hydroxyethyl)-aminobenzene, and 4-amino-3-methyl phenol, or the water-soluble salts thereof; examples for coupling substances are resorcinol, 2-methyl resorcinol, 4-chlororesorcinol, 2-amino-4-chlorophenol, 4-(N-methyl) aminophenol, 2-aminophenol, 3-aminophenol, 1-N-2-hydroxy-4-aminobenzene, 3-N,N-dimethyl aminophenol, 5-amino-2-methyl phenol, 3-amino-2-methyl amino-6-methoxypyridine, 2-amino-3-hydroxypyridine, 4-aminodiphenyl amine, 4,4'-diaminodiphenyl amine, 2-dimethyl amino-5-aminopyridine, 2,6-diaminopyridine, 1,3-diaminobenzene, 1-amino-3-(2'-hydroxyethyl amino)

benzene, 1-amino-3-[bis(2'-hydroxyethyl)amino] benzene, α-naphthol, 1,4-diamino-2-chlorobenzene, 4,6-dichlororesorcinol, 1,3-diaminotoluene, 4-hydroxy-1,2-methylene dioxybenzene, 1,5-dihydroxynaphthaline, 1,7-dihydroxy-naphthaline, 2,7-dihydroxynaphthaline, 1-hydroxynaphthaline, 2,4-diamino-3-chlorophenol, and/or 1-methoxy-2-amino-4-(2'-hydroxyethyl amino) benzene, whereby this list of examples is not complete.

Developing and coupling substances are preferably contained in a molar proportion of 1:3 to 5:1, in particular about 1:1 and about 3:1; their proportion in the hair dyeing compositions used according to the invention may range from about 0.25% to about 5% by weight, depending on the desired coloration.

The oxidizing agent used are in particular 2% to 12% hydrogen peroxide solutions, emulsions or gels.

The oxidation dyestuff compositions can be used as solutions, creams, pastes, gels, aerosols, etc.

Application is carried out by mixing the two Compositions A and B, whereby the weight proportion ranges from about 2:1 and 1:4, depending on the hydrogen peroxide concentration.

The following Examples illustrate the invention.

EXAMPLE 1

20 g of an oxidation dyestuff precursor Composition A, composed of

| | |
|---|---|
| Cetyl stearyl alcohol | 10.00 (% by wt.) |
| Coco fatty acid monoethanolamide | 2.00 |
| Stearic acid monoethanolamide | 2.00 |
| Stearic acid diethanolamide | 1.00 |
| p-Toluylenediamine sulfate | 0.25 |
| m-Aminophenol | 0.01 |
| Resorcinol | 0.01 |
| p-Aminophenol | 0.08 |
| p-Amino-o-cresol | 0.06 |
| Picramic acid | 0.05 |
| Monoethanolamine | 3.20 |
| Ammonium chloride | 0.20 |
| Sodium lauryl sulfate | 0.30 |
| Manganese(IV)oxide | 0.06 |
| Sodium sulfite | 0.25 |
| Ethylene diaminotetraacetic acid | 0.20 |
| Perfume | 0.20 |
| Water | ad 100.00 | showing a pH-value of 9.8, are mixed with 40 g of a 2% hydrogen peroxide solution of the following Composition (B)

| | |
|---|---|
| Hydrogen peroxide | 2.00 (% by wt.) |
| Polyoxyethylene polyoxypropylene copolymer (Poloxamer$^R$) | 1.00 |
| Triethanolamine lauryl ether sulfate | 0.70 |
| PEG-7-glyceryl cocoate | 0.50 |
| 1-Hydroxyethane-1,1-diphosphonic acid | 0.25 |
| Water | ad 100.00 | having a pH-value of 2.9, and the mixture, which had a pH-value of 9.6, was applied to ash-blond human hair.

After 20 minutes processing the hair was rinsed, washed and dried.

An expressive, hazelnut-blond coloration was obtained.

Omission of the HEDP resulted in an intensive reaction upon admixture of the Compositions A and B, which did not permit even application onto the hair due to excessive formation of foam, consequently also failing to lead to a satisfactory coloration.

EXAMPLE 2

An oxidation dyestuff precursor Composition A, consisting of

| | |
|---|---|
| Cetyl stearyl alcohol | 10.00 (% by wt.) |
| Coco fatty acid monoethanolamide | 2.00 |
| Stearic acid monoethanolamide | 2.00 |
| Stearic acid diethanolamide | 1.00 |
| p-Toluylenediamine sulfate | 0.50 |
| p-Amino-o-cresol | 0.40 |
| p-Aminophenol | 0.10 |
| Monoethanolamine | 6.20 |
| Ammonium chloride | 0.20 |
| Sodium lauryl sulfate | 0.30 |
| Copper-II-chloride | 0.0004 |
| Iron-III-oxide | 0.000 |
| Sodium sulfite | 0.25 |
| Ethylene diaminotetraacetic acid | 0.20 |
| Perfume | 0.20 |
| Water | ad 100.00 | which showed a pH-value of 10.3, was mixed in a weight proportion of 1:1 with a hydrogen peroxide Composition B, consisting of

| | |
|---|---|
| Hydrogen peroxide | 6.0 (% by wt.) |
| Cetyl stearyl alcohol | 1.80 |
| Sodium lauryl sulfate | 0.20 |
| 1-Hydroxyethane-1,1-diphosphonic acid | 0.30 |
| Salicylic acid | 0.10 |
| Water | ad 100.00 | having a pH-value of 2.0, and the mixture applied to medium blond hair (pH-value: 10.0).

After 20 minutes processing, rinsing and drying, the hair was showed a strong, glossy red coloration.

Omission of the 1-hydroxyethane-1,1-diphosphonic acid led to an intense, foaming reaction upon admixing of Compositions A and B.

EXAMPLE 3

An oxidation dyestuff precursor Composition A, consisting of

| | |
|---|---|
| Cetyl stearyl alcohol | 10.00 (% by wt.) |
| Coco fatty acid monoethanolamide | 2.00 |
| Stearic acid monoethanolamide | 2.00 |
| Stearic acid diethanolamide | 1.00 |
| p-Toluylenediamine sulfate | 0.20 |
| p-Aminophenol | 0.70 |
| p-Amino-o-cresol | 0.70 |
| Monoethanolamine | 4.00 |
| Ammonium chloride | 0.20 |
| Sodium lauryl sulfate | 0.30 |
| Potassium iodide | 0.04 |
| Magnanese-IV-oxide | 0.05 |
| Sodium sulfite | 0.12 |
| Ethylene diaminotetraacetic acid | 0.20 |
| Perfume | 0.20 |
| Water | ad 100.00 | with a pH-value of 10.0 was mixed in a weight proportion of 1:2 with a hydrogen peroxide Composition B, consisting of

| | |
|---|---|
| Hydrogen peroxide | 4.0 (% by wt.) |
| Polyoxyethylene polyoxypropylene copolymer (Poloxamer®) | 1.0 |
| Triethanolamine lauryl ether sulfate | 0.7 |
| PEG-7-glyceryl cocoate | 0.5 |
| 1-Hydroxyethane-1,1-diphosphonic acid | 0.3 |
| Water | ad 100.00 | having a pH-value of 2.9, and the resulting mixture (pH-value: 9.7) was applied to ash-blond hair. After twenty minutes processing, rinsing and drying, an intensive copper-red coloration was obtained.

Omission of the HEDP resulted in an intense reaction upon admixture of Compositions A and B, which prevented an even coloration.

What is claimed is:

1. Process for the oxidative dyeing of human hair, whereby an aqueous composition (AB) having a pH-value between 9.0 and 12.0 is applied to the hair, wherein the composition (AB) was obtained by admixture of an oxidation dyestuff precursor Composition (A) having a pH of at least 9.0 and which comprises at least one developing and at least one coupling substance, and further comprising one or more metal compounds, selected from manganese dioxide, potassium iodide, sodium iodide, lithium chloride, calcium chloride, calcium nitrate, magnesium chloride, magnesium acetate, barium nitrate, barium chloride, copper(II) chloride, copper(II) sulfate, cobalt chloride, iron oxide, iron chloride, cerium sulfate, vanadium sulfate, potassium bichromate and/or sodium bichromate, having an alkaline pH-value, with a hydrogen peroxide Composition(B), having a pH-value in the acidic range and comprising 0.05 to 5.0% by weight, calculated to the total composition, of 1-hydroxyethane-1,1-diphosphonic acid and/or the alkali or ammonium salts thereof.

2. Process according to claim 1, wherein the hydrogen peroxide Composition (B) has a pH-value of 1.5 to 5.

3. Process according to claim 2, wherein the hydrogen peroxide Composition (B) has a pH-value of 2 to 4.

4. Composition for the oxidative dyeing of human hair, consisting of two aqueous Compositions A and B stored separately until application, whereby the Composition A comprises a pH of at least 9.0 and at least one developing and one coupling substance, and further comprising at least one or more metal compounds, selected from manganese dioxide, potassium iodide, sodium iodide, lithium chloride, calcium chloride, calcium nitrate, magnesium chloride, magnesium acetate, barium nitrate, barium chloride, copper (II) chloride, copper(II) sulfate, cobalt chloride, iron oxide, iron chloride, cerium sulfate, vanadium sulfate, potassium bichromate and/or sodium bichromate having an alkaline pH-value, and the Composition B comprises hydrogen peroxide and 0.1% to 5% by weight, calculated to the total composition, of 1-hydroxy-ethane-1, 1-diphosphonic acid and/or the alkali or ammonium salts thereof having an acidic pH-value, whereby mixing of these Compositions A and B results in a hair-dyeing composition with a pH-value between 9.0 and 12.0.

5. Process according to claim 1, comprising manganese dioxide as metal compound.

6. Process according to claim 1, containing potassium or sodium iodide as metal compound.

7. Process according to claim 1, comprising copper(II) chloride and/or copper(II) sulfate as metal compound.

8. Process according to claim 1, containing calcium chloride and/or calcium nitrate as metal compound.

9. Composition according to claim 1, comprising manganese dioxide as metal compound.

10. Composition according to claim 1, containing potassium or sodium iodide as metal compound.

11. Composition according to claim 1, comprising copper (II) chloride and/or copper(II) sulfate as metal compound.

12. Composition according to claim 1, containing calcium chloride and/or calcium nitrate as metal compound.

13. The process of claim 1, wherein the pH of composition (AB) is greater than about 9.0.

14. The composition of claim 1, wherein the pH of the composition for oxidative hair dyeing is greater than about 9.0.

\* \* \* \* \*